(12) United States Patent
Miura et al.

(10) Patent No.: US 8,232,445 B2
(45) Date of Patent: Jul. 31, 2012

(54) ABSORBENT ARTICLE COMPRISING CONDENSED TANNIN

(75) Inventors: Tsunetoshi Miura, Kobe (JP); Raphael Warren, Amberly Village, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1195 days.

(21) Appl. No.: 11/509,475

(22) Filed: Aug. 24, 2006

(65) Prior Publication Data

US 2007/0049887 A1 Mar. 1, 2007

Related U.S. Application Data

(60) Provisional application No. 60/711,263, filed on Aug. 25, 2005.

(51) Int. Cl.
*A61F 13/15* (2006.01)
*A61F 13/20* (2006.01)

(52) U.S. Cl. ......... 604/359; 604/360; 424/765; 424/777

(58) Field of Classification Search .................. 604/367, 604/368, 359, 360; 424/725, 765, 771, 774, 424/777

See application file for complete search history.

(56) References Cited

U.S. PATENT DOCUMENTS

| | | | |
|---|---|---|---|
| 4,681,757 A | 7/1987 | Mimasu et al. | |
| 5,085,654 A * | 2/1992 | Buell | 604/370 |
| 5,994,413 A | 11/1999 | Tanabe et al. | |
| 6,139,842 A | 10/2000 | Matsuda et al. | |
| 6,765,124 B2 | 7/2004 | Wada et al. | |
| 7,166,307 B1 | 1/2007 | Ahn et al. | |
| 2003/0082219 A1 | 5/2003 | Warren et al. | |
| 2003/0206943 A1 | 11/2003 | Hammons et al. | |
| 2004/0170589 A1 | 9/2004 | Gatto | |
| 2005/0129651 A1 | 6/2005 | Gatto et al. | |
| 2005/0148962 A1 | 7/2005 | Warren et al. | |
| 2005/0154362 A1 | 7/2005 | Warren et al. | |
| 2006/0062816 A1 | 3/2006 | Gatto et al. | |

FOREIGN PATENT DOCUMENTS

| | | |
|---|---|---|
| DE | 36 22 896 A1 | 1/1988 |
| GB | 2 092 006 A | 8/1982 |
| JP | 64-025726 | 1/1989 |
| JP | 2961555 | 12/1990 |
| JP | 3-61457 | 9/1991 |
| JP | 03-268751 | 11/1991 |
| JP | 03-268751 A | 11/1991 |
| JP | 6-69933 | 9/1994 |
| JP | 07-187993 | 7/1995 |
| JP | 09-271484 | 10/1997 |
| JP | 09-315985 A | 12/1997 |
| JP | 09-315992 A | 12/1997 |
| JP | 11-116829 | 4/1999 |
| JP | 2000-303194 A | 10/2000 |
| JP | 2000-303250 | 10/2000 |
| JP | 2002-097187 A | 4/2002 |
| JP | 2003-052746 | 2/2003 |
| JP | 2004-089234 | 3/2004 |
| JP | 2004-092008 | 3/2004 |
| WO | WO 01/03748 A1 | 1/2001 |

OTHER PUBLICATIONS

Hagerman, A. "Tannin Chemistry: Condensed Tannin Chemistry", 2002, p. 3.*
English translation of JP 09-271484 to Kake.*
International Search Report dated Apr. 13, 2007.
Product Catalog for Pancil by Rilis Scientific Industry Co., Ltd.

* cited by examiner

*Primary Examiner* — Melanie Hand
(74) *Attorney, Agent, or Firm* — Andres E. Velarde

(57) ABSTRACT

An absorbent article comprising a condensed tannin. The condensed tannin is extracted from a plant family which is selected from the group consisting of Ebenacea, Mimosoideae, Apiaceae, Pinaceae, Rosaceae, Fagaceae, and mixtures thereof.

20 Claims, No Drawings

US 8,232,445 B2

ABSORBENT ARTICLE COMPRISING CONDENSED TANNIN

CROSS REFERENCE TO RELATED APPLICATION

This application claims the benefit of U.S. Provisional Application No. 60/711,263, filed Aug. 25, 2005.

FIELD OF THE INVENTION

The present invention relates to absorbent articles to be worn in contact with body of wearer, in particular to absorbent articles such as pantiliners, sanitary napkins, tampons, interlabial pads, incontinent pads, diapers, breast pads, perspiration pads. More particularly, the present invention relates to an absorbent article comprising a condensed tannin.

BACKGROUND OF THE INVENTION

Absorbent articles, such as sanitary napkins, pantiliners, and incontinence pads, are typically worn in the crotch region of an undergarment. These devices are designed to absorb and retain liquids and other discharges from the human body to prevent body and garment soiling. The absorbent articles are typically placed in a garment such as the wearer's panty and worn between the wearer's legs, adjacent to the genital (or fluids discharge source) area of the body. Disposable absorbent articles generally comprise a fluid-permeable topsheet, an absorbent core, and a fluid-impermeable backsheet.

Recently, research has focused on removal of foul odors and prevention of skin diseases. Many bodily fluids tend to have an unpleasant odor (or malodor), or develop such an odor when in contact with air and/or bacteria for prolonged periods. Additionally, urine and/or other exudates absorbed into the absorbent article are converted to ammonia by urease produced by skin-flora, i.e., a group of normal microorganisms on the body. This ammonia, in turn, may cause dermatitis, rash and/or other forms of skin irritation. It is known that such disease of the skin can be a serious medical matter.

Antimicrobial materials and bactericides in general are chemical compositions that are used to prevent microbiological contamination and deterioration of products, materials, and systems. Such antimicrobial materials and bactericides can also effectively work as an odor control material for the removal or reduction of foul odors developed from disposable absorbent articles which has already absorbed body fluids. However, depending on the nature or characteristics of antimicrobial materials or bactericides in disposable absorbent articles, it is found that such antimicrobial materials and bactericides tend to affect skin health. In particular, many of these materials, by having antimicrobial activity, can alter the normal distribution of body flora. Therefore, care must be taken in the selection and use of these materials so as to avoid disrupting the normal flora on the body.

Japanese Patent No. 2938507 discloses a paper diaper which includes, in an absorbent material, a polyphenol organic compound which is selected from a group consisting of a tannin, a tannin acid, a galla rhois, a gallnut, and a gallic acid, which are extracted from plants. The polyphenol organic compound is included in an absorbent material. This publication states that the diaper disclosed provides a good remedy against diaper rash (and thus, a good skin friendliness nature), however, it does not seem to provide enough odor control function which is necessary for paper diapers.

International Publication No. WO 01/03748 discloses a sanitary napkin which includes a galla rhois-containing composition and a herb medicine applied thereto for removal of odor. The sanitary napkin disclosed seems to have odor control function, however, the galla rhois has been reported to generate skin rash, and thus may not be appropriate, in particular for direct exposure to the normally sensitive woman's vulva or vaginal areas.

Thus, there is a need for an absorbent article that has an improved odor control function while maintaining body comfort and body protection against the wearer's body.

SUMMARY OF THE INVENTION

The invention is directed to an absorbent article comprising a condensed tannin. The condensed tannin is extracted from a plant family which is selected from the group consisting of Ebenacea, Mimosoideae, Apiaceae, Pinaceae, Rosaceae, Fagaceae, and mixtures thereof.

Since the condensed tannin has more hydroxyl groups and larger molecular structure than general polyphenol organic compounds, it can trap malodor molecules more effectively than the general polyphenol organic compounds. This advantage provides flexibility for its placement in an absorbent article, i.e., it could be applied to the topsheet or the absorbent core, or it could be transferable to the body of wearer. In addition, since the condensed tannin is extracted from the plant family, more commercial sources of a desirable condensed tannin structure will be available to manufacture the product and provide the desired benefit. Further, the absorbent article of the invention can also provide a body treatment that protects the wearer's body and provides body comfort.

The foregoing answers the need for an absorbent article that has an improved odor control function while maintaining body comfort and body protection.

These and other features, aspects, and advantages of the present invention will become evident to those skilled in the art from reading of the present disclosure.

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges such as body fluids, and is intended to include pantiliners, sanitary napkins, tampons, interlabial pads, incontinent pads, diapers, breast pads, perspiration pads. The absorbent articles include (or are formed by) a lot of component materials such as fibers, sheet (including film) materials, layered materials, adhesives, absorbent materials, and the like.

Herein, "disposable article" refers to articles which are intended to be discarded after a single use, composted, or otherwise disposed of in an environmentally compatible manner. (That is, they are not intended to be laundered or otherwise restored or reused as an absorbent article.) Herein, "component fibers" refers to fibers which form a material (i.e., a topsheet material, a backsheet material, or an absorbent core material) of the absorbent article. The component fibers can be natural fibers (e.g., wood or cotton fibers), modified natural fibers, synthetic fibers (e.g., thermoplastic fibers such as polyester, polypropylene, or polyethylene fibers), or combinations thereof.

Preferred component fibers for the topsheet are thermoplastic fibers. Preferred component fibers for the absorbent core are natural fibers (e.g., wood or cotton fibers) or a mixture of natural fibers and thermoplastic fibers.

Herein, "body surface" refers to surfaces of absorbent articles and/or their component materials which face the body of the wearer, while "garment surface" refers to the opposite surfaces of the absorbent articles and/or their component materials that face away from the wearer when the absorbent articles are worn. Absorbent articles and components thereof, including the topsheet, backsheet, absorbent core, and any individual layers of their component materials, have a body surface and a garment surface.

Herein, "body" refers to outer layers formed by mammalian epidermal tissues including the skin and hair. The characteristics of the body tend to differ dramatically depending on the position, age, sex, and individual's nature. For example, the skin of babies and young children differs from the skin of adults, and the skin having hair differs from the non-haired skin.

The absorbent article has two surfaces, a liquid previous body surface (or "body-contacting surface") and a liquid impervious garment surface (or "garment-contacting surface"). The body surface of the absorbent article is intended to be worn adjacent to the body of the wearer. The garment surface of the absorbent article is on the opposite side and is intended to be placed adjacent to the wearer's undergarments when the absorbent article is worn.

Herein, "a surface treated with a chemical agent" refers to at least a part of a surface of materials or articles (e.g., fibers, sheet materials, absorbent articles) wherein the chemical agent is incorporated therein by spraying, dipping, printing, or soaking so that the chemical agent is coated onto or otherwise attached or bound thereto.

The present invention is employed in disposable absorbent articles, preferably in pantiliners, sanitary napkins, tampons, interlabial pads, and incontinent pads.

Condensed Tannin

The condensed tannin of the invention is extracted from a plant family which is selected from the group consisting of Ebenacea, Mimosoideae, Apiaceae, Pinaceae, Rosaceae, Fagaceae, and mixtures thereof. These plant families include the following genera and species:

(a) Family Ebenacea, Genus *Diosyros*, Species *Persimmon*
(b) Family Mimosoideae, Genus *Mimosa*
(c) Family Apiaceae, Genus *Pastinaca*, Species *Sativa*
(d) Family Apiaceae, Genus *Daucus*, Species *Carota*
(e) Family Pinaceae, Genus *Tsuga*, Species *Hemlock*
(f) Family Pinaceae, Genus *Picea*
(g) Family Pinaceae, Genus *Pinus*
(h) Family Rosaceae, Genus *Malus*
(i) Family Fagaceae, Genus *Quercus*, Species *Oak*

In one embodiment, the condensed tannin is extracted from a persimmon which belongs to Species Persimmon (hereinafter referred to as "persimmon tannin"). It is believed that the persimmon tannin has the following structure:

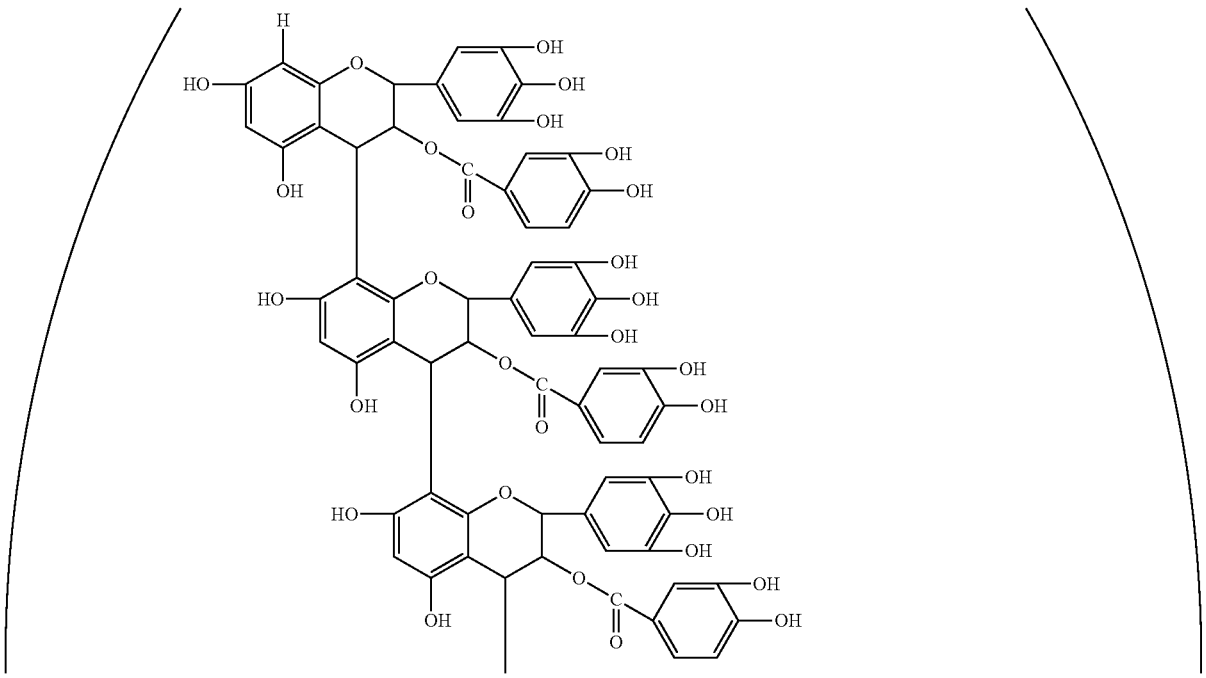

-continued

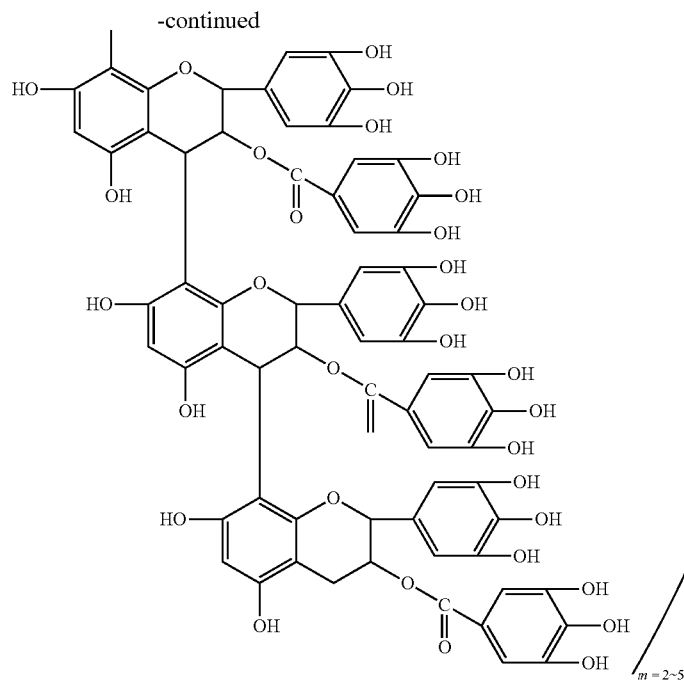

One agent which contains a persimmon tannin is available from Rilis Scientific Industry Co., Ltd., Osaka, Japan, under Code No. Pancil COS-6A.

In another embodiment, the condensed tannin is extracted from an apple (or pumila) which belongs to Genus Malus (hereinafter referred to as "apple tannin"). The apple tannin is has the following general formula and structure:

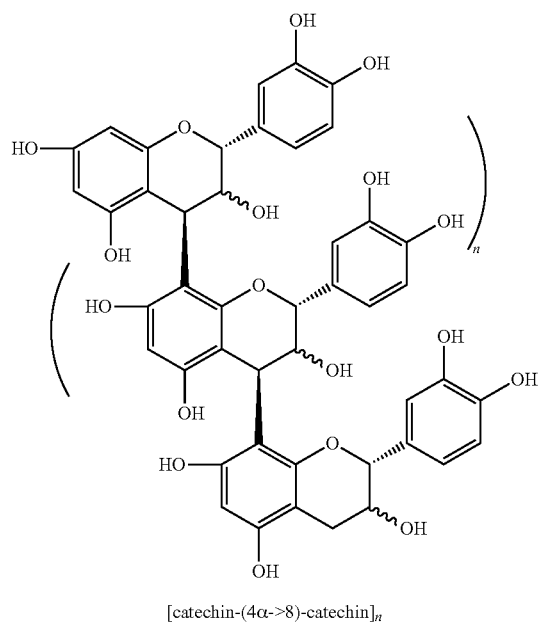

[catechin-(4α->8)-catechin]$_n$

One agent which contains an apple tannin is available from Asahi Food & Health Care Ltd., Tokyo, Japan, under Code No. ApplePhenon.

If desired, the condensed tannin of the invention can further contain other extracted material(s) from the same plant or the other plants. Such extracted materials include, but not limited to, other polyphenol organic compounds than the condensed tannin, such as hydrolyzable tannins, flavonols, and the like.

Carrier Material

The condensed tannin for use in the absorbent article of the invention can be water-soluble or lipid-soluble and can be incorporated into the absorbent article in the form of a particle (including a flake), a solution, a suspension, a dispersion, an emulsion or the like. The condensed tannin can be incorporated into the absorbent article directly (i.e., without a carrier material) or indirectly (i.e., together with a carrier material).

The absorbent article may further include a carrier material for the condensed tannin. In certain embodiments, the condensed tannin is incorporated into the carrier material, and then the carrier material is incorporated into the absorbent article. Herein, "carrier material" is a material which should not interfere with the effect of the condensed tannin nor substantially affect the normal function of the various structures of the absorbent article. The primary function of the carrier material is to convey the condensed tannin to the absorbent article. Carrier materials for the condensed tannin can include compositions that are in the form of lotions, creams, oils, ointments, powders, foams, or gels and the like.

Typical carrier materials for the condensed tannins include aqueous or alcoholic solutions, oils and fats such as hydrocarbon oils, fatty acid esters, long chain alcohols and silicone oils, finely divided solids such as starch or talc and the like. The condensed tannins is preferably dissolved, suspended or emulsified in the carrier material.

A. Component Treatment Material

In certain embodiments, the carrier material is a component treatment material for the component material(s) of absorbent article. Herein, "component treatment material" refers to materials which are used to control the physical property of the component material(s) of the absorbent article. Such a component treatment material is expected to remain at the component material(s) of the absorbent article without transferring to other portion(s) of the absorbent article nor the wearer's body. Suitable component treatment materials include finishing oils for controlling friction at a surface of component fibers, surfactant materials for controlling hydrophilicity at a surface of film materials or for component fibers, and the like. In one embodiment, the carrier material is a finishing oil of component fibers for a nonwoven material which forms a part of the absorbent article (e.g., a nonwoven topsheet). In this embodiment, the condensed tannin is dissolved, suspended or emulsified in the finishing oil and incorporated into the absorbent article together with the finishing oil.

B. Body Treatment Material

In an alternative embodiment, the carrier material is a body treatment material (or composition) for the wearer's body which delivers the condensed tannin to at least a portion of the body of the wearer of the article. Herein, "body treatment material" refers to materials or compositions that when applied topically to the body are capable of preventing, reducing, and/or eliminating any occurrence of body disorders, particularly skin disorders associated with erythema, malodor, itch and bacterial infections. Hereinafter, "body treatment material" also refers to as "body treatment composition". Herein "skin disorders" refers to symptoms associated with irritating, acute, or chronic skin abnormalities. Examples of such symptoms include, but are not limited to, itching, inflammation, rash, burning, stinging, redness, swelling, sensitivity, sensation of heat, flaking/scaling, malodor, and the like. Suitable body treatment materials are in the form of lotions, creams, oils, ointments, powders, foams, or gels and the like.

The condensed tannin can be incorporated into any body treatment material known in the art. The body treatment material can contain any ingredients commonly used in the art. Such body treatment material can also facilitate (directly or indirectly) the transfer of the condensed tannin to the body of the wearer of the absorbent article for perception of body care sensation by the wearer of the absorbent article. The body treatment material can contain the condensed tannin in the form of a particle (including a flake), a solution, a suspension, a dispersion, an emulsion or the like in a carrier material such as a solution, suspension, dispersion, emulsion or composition.

In one embodiment, the body treatment material which incorporates the ondensed tannin is delivered or transferred directly or indirectly to the body of the wearer during normal use of the absorbent article. As a result, the condensed tannin is also transferred automatically to the wearer's body, as a function of the body treatment material, by the normal contact, wearer motion and/or body heat during the wear of the absorbent article.

When released from the body treatment material the condensed tannin is free to migrate from the location of the body treatment material in the absorbent article to the body and/or mucosal surface of the wearer. The body treatment material can be incorporated into a component of any portion or portions of the absorbent article including, but not limited to, in the topsheet, the backsheet, the absorbent core, the wings, the leg cuff, the side panel, the waist region, the fastener, and any other layer(s) within or adjacent to the absorbent core. The body treatment material may be positioned in proximity to the wearer's body and, may be a component of a body-contacting surface of portions of the absorbent article such as the topsheet, wings, side panels, leg cuffs, waist region, fasteners, and the like.

When the condensed tannin is released by the body treatment material, it may be in an active functional form such as in a solution, dispersion, suspension, emulsion or the like. If it is in a non-functional form such as a powder, wax, flake or particulate form, it should be activated by a contact with moisture of body fluids such as menses, urine and feces. The types of body treatment materials that are useful in the absorbent articles of the invention for facilitating automatic transfer of the condensed tannin from any portion of the absorbent article to the body and/or mucosal surface of a wearer will be readily apparent to those skilled in the art.

Regardless of the body treatment material employed, the condensed tannin or condensed tannin containing composition upon release can migrate from its original location, i.e., it can be moved by the flow of body fluid, by motion of the wearer, by pressure and the like, or because of a decrease in viscosity upon exposure to body heat, to other regions in the absorbent article. Condensed tannins that are hydrophilic or are incorporated into carrier materials that are hydrophilic can migrate throughout hydrophilic structures of the absorbent article, such as through hydrophilic pores or other openings that allow body fluid to flow from the topsheet to the core.

The body treatment material contains relatively low concentrations of a select combination of body treatment agents that are capable of reducing and eliminating the occurrence of skin disorders that can result from contact between the body and moisturized component material(s), skin disorders resulting from prolonged moist human tissue that can occur from the body being exposed to moisture or other body exudates, and/or skin disorders that are generated from contact between the body and microbial or bacterial agents. Herein, "select combination of body treatment agents" refers to the following combinations: (a) hexamidine, zinc oxide, and niacinamide; (b) hexamadine and zinc oxide; and (c) hexamadine and niacinamide. Preferred select combination of skin treatment agents are disclosed in, for example, International Pub. No. WO 03/028776 published on Apr. 10, 2003 and U.S. Patent Application Pub. No. 20030206943 published on Nov. 6, 2003.

C. Optional Components

If desired, other optional components which are suitable for body treatment can be added to or as the body treatment material. Nonlimiting examples of such optional components include allantoin; aluminum hydroxide gel; calamine; cysteine hydrochloride; racemic methionine; sodium bicarbonate; Vitamin C and derivatives thereof; protease inhibitors including serine proteases, metalloproteases, cysteine proteases, aspartyl proteases, peptidases, and phenylsulfonyl fluorides; lipases; esterases including diesterases; ureases; amylases; elastases; nucleases; guanidinobenzoic acid and its salts and derivatives; herbal extracts including chamomile; and mixtures thereof. Guanidinobenzoic acid and its salts and derivatives are more fully described in U.S. Pat.No. 5,376,655, issued to Imaki et al. on Dec. 27, 1994. These other suitable skin treatment actives are typically included at concentrations ranging from about 0.001% to about 10% by weight of the lotion composition. These and other optional components (including preferred carrier materials for the body treatment material) which are suitable for body treatment are disclosed in WO 03/028776 and U.S. Patent Pub. No. 20030206943.

In one embodiment, the body treatment material is an emollient-containing composition containing various emollients that are delivered directly from the skin-contacting surface to the wearer's body to perform an immediate and sustained body care sensation while maintaining or even improving skin health.

The condensed tannins may be dissolved, suspended or emulsified components of emollient-containing compositions that can be positioned anywhere in the absorbent articles. For example, the condensed tannins may be incorporated into a body-contacting surface of the absorbent articles, such as the topsheet, wings, leg cuff, fastening device and the like of hygienic disposable absorbent articles.

In one embodiment, the emollient-containing composition comprises from about 0.1% to about 20%, from about 0.3% to about 10%, or from about 0.5% to about 5% by weight of the condensed tannin or mixture thereof, and from about 99.9% to about 80%, from about 99.7% to about 90%, or about 99.5% to about 95% by weight of the emollient or mixture thereof.

In addition to its function as a delivery or transfer means, the emollient-containing composition is particularly beneficial to the body since it improves or reduces body friction and softness, and hence maintains or even improves skin health. Suitable emollients to be used herein assure a film-forming capacity on the body and helps to protect and reduce the occurrence of skin itching or burning. Suitable emollients to be used herein are also able to locate themselves between the layers of the skin epidermis, thereby enhancing the elastic properties of the skin.

Other suitable skin treatment materials are disclosed in, for example, U.S. Pat. No. 5,643,588, issued to Roe et al. on Nov. 28, 1994; U.S. Pat. No. 5,635,191, issued to Roe et al. on Nov. 28, 1994; U.S. Pat. No. 6,515,029, issued to Krzysik et al. on Apr. 23, 1999; U.S. Pat. No. 6,475,197, issued to Krzysik et al. on Apr. 24, 1999; U.S. Pat. No. 6,149,934, issued to Krzysik et al. on Apr. 23, 1999; U.S. Pat. No. 6,749,860, issued to Tyrrell et al. on Dec. 22, 2000; U.S. Pat. No. 6,551,607, issued to Minerath et al. on Dec. 29, 1999; U.S. Pat. No. 6,689,932, issued to Kruchoski et al. on Dec. 21, 2001; U.S. Pat. Pub. No. 20020040210 Al, published on Apr. 4, 2002; and International Pub. No. WO 2004/061171, published on Jul. 22, 2004.

Incorporation

The condensed tannin employed in the absorbent articles of the invention is incorporated into the absorbent article in a configuration that does not substantially affect the normal function of the various structures of the absorbent article (e.g., the liquid pervious nature of the topsheet, the absorbency of the core, and the like for absorbent articles).

The condensed tannin can be incorporated into any portion or portions of the absorbent article including, but not limited to, in the topsheet, the backsheet, the absorbent core, the wings, the leg cuff, the side panel, the waist region, the fastener, and any other layer(s) within or adjacent to the absorbent core. The condensed tannin may be positioned in proximity to the wearer's skin and may be located at a skin-contacting surface of the absorbent article.

The condensed tannin, whether or not it is incorporated into a carrier material, can be uniformly or non-uniformly distributed throughout the absorbent article and/or onto the surface of one layer or several layers of the absorbent article.

The condensed tannin can be incorporated into a component material(s) of the absorbent article either before or during the manufacture of the absorbent article.

The condensed tannin may be incorporated into a component material(s) of the absorbent article before the manufacture of the absorbent article, and then the component material(s) containing the condensed tannin is incorporated into the absorbent article in the manufacture process for the absorbent article. In one embodiment, the condensed tannin is incorporated into the topsheet material (e.g., a nonwoven material or a formed film material) by spraying, dipping, printing, or soaking so that the condensed tannin is coated onto or otherwise attached or bound to the topsheet material. In another embodiment where the topsheet is formed by a nonwoven material, the condensed tannin can applied to the component fibers of the nonwoven material by spraying, dipping, printing, or soaking before the formation of the nonwoven material. The component fibers are joined together to form the nonwoven material through a conventional nonwoven formation process known in the art (e.g., a card process). After the formation of the nonwoven material, it is joined to other component materials to form the absorbent article in the manufacture process.

In an alternative embodiment the condensed tannin is incorporated into the absorbent article during the manufacture process for the absorbent article. For example, the condensed tannin (preferably together with a carrier material) is incorporated onto at least a part of the body-contacting surface of the topsheet which is typically formed by a nonwoven or an apertured formed film, preferably after the topsheet is joined to other component materials to form the absorbent article. If desired, the condensed tannin can be incorporated into the backsheet, and/or the absorbent core materials; or other components of the absorbent article during the manufacture process. For example, the condensed tannin together with a carrier material can be applied, after being dispersed in a liquid or semi-solid carrier material, to the topsheet, to the absorbent core, or to the backsheet, by coating, extruding, spraying, dipping, printing, or soaking.

The Absorbent Article

The absorbent article of the present invention generally comprises at least three primary components, i.e., a topsheet; a backsheet; an absorbent core. The topsheet, backsheet, and absorbent core can comprise any types of component materials known in the art as being suitable for such components such as fibers, sheet (including film) materials, layered materials, adhesives, absorbent materials, and the like.

Generally, at least one of the topsheet, the backsheet and the absorbent core includes the condensed tannin. In one embodiment, the condensed tannin which may be in the form of a particle (including a flake), a solution, a suspension, a dispersion, an emulsion or the like is incorporated into one of the component materials of the absorbent article directly (i.e., without a carrier material).

In another embodiment, at least one of the topsheet, the backsheet and the absorbent core includes component fibers or a sheet material (including a film material). In such embodiments, the component fibers may have a surface treated with the condensed tannin. For example, the component fibers of the topsheet (or the absorbent core) have a surface treated with the condensed tannin. Alternatively, the component fibers can contain a thermoplastic material which contains the condensed tannin.

In another embodiment, at least one of the topsheet, the backsheet and the absorbent core includes a sheet material having a surface treated with the condensed tannin. For example, the film material of the topsheet can have a surface treated with the condensed tannin.

A. Topsheet

The absorbent article may comprise any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the body of the wearer. The topsheet, while being capable of allowing rapid transfer of fluid through it, also provides for the transfer or migration of the body treatment material (if it is used as a carrier material) onto an external or internal portion of a wearer's body. A suitable topsheet can be made of various materials such as woven and nonwoven materials; apertured film materials including apertured formed thermoplastic films, apertured plastic films, and fiberentangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,324,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Non-limiting examples of woven and nonwoven materials suitable for use as the topsheet include fibrous materials as component fibers made from natural fibers, modified natural fibers, synthetic fibers, or combinations thereof. Suitable component fibers for the topsheet are thermoplastic fibers. Suitable thermoplastic fibers can be made from a single polymer (monocomponent fibers), or can be made from more than one polymer (e.g., bicomponent fibers). Herein, "bicomponent fibers" refers to thermoplastic fibers that include a core fiber made-from one polymer that is encased within a thermoplastic sheath made from a different polymer. The polymer forming the sheath often melts at a different, typically lower, temperature than the polymer forming the core. As a result, these bicomponent fibers provide thermal bonding due to melting of the sheath polymer, while retaining the desirable strength characteristics of the core polymer. Suitable bicomponent fibers for use in the absorbent article can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene core, and a lower melting polyethylene sheath.

These fibrous materials can be either hydrophilic or hydrophobic, but it is often desirable for the topsheet be hydrophobic or rendered hydrophobic. Any portion or the entirety of the topsheet can be rendered hydrophilic or hydrophobic, as desired, by the use of any known method for making the topsheet hydrophilic or hydrophobic components.

In one embodiment, the component fibers of the topsheet have a surface treated with the condensed tannin. One method for this treatment is a touch roll process known in the art. In this process, one half of a rotating roll is dipped in a solution of the condensed tannin, while the other half of the roll contacts fibers thereby applying the solution to the fibers. Fibers having a surface treated with the condensed tannin are available from Chisso Corporation, Tokyo, Japan, under Code No. XESC4245SDL. Other methods for treating a surface of the component fibers with the condensed tannin are disclosed in U.S. Pat. No. 6,197,322 issued to J. Dutkiewicz et al., on Mar. 6, 2001.

When the topsheet includes (or is formed by) a nonwoven material (i.e., a nonwoven web), the nonwoven web may be produced by any known procedure for making nonwoven webs, nonlimiting examples of which include spunbonding, carding, wet-laid, air-laid, meltblown, needle-punching, mechanical entangling, thermomechanical entangling, and hydroentangling. A suitable nonwoven web for the topsheet is produced by a carded thermal bonding process (or an air-thru process) which is available from Kang Na Hsiung Enterprise Co., Ltd. (KNH), a Taiwan company, under Code No. AT018-CS15-0.

B. Backsheet

The backsheet can be any known or otherwise effective backsheet material. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof. The backsheet may have a thickness of from about 0.012 mm (0.5 mil) to about 0.081 mm (3.4 mils).

In one embodiment, the backsheet is a single layer polyethylene film which is available from Huahan, Guangdong, China, under Code No. KH-Y-02-D06.

In an alternative embodiment, the backsheet has a microporous structure which can permit vapors to escape from the absorbent core (often called "breathable backsheet") while still preventing body fluids from passing through the backsheet. A suitable microporous polyethylene film is available from Mitsubishi Plastics. Inc., Tokyo, Japan, under Code No. RN-13.

C. Absorbent Core

The absorbent core is typically positioned between the topsheet and the backsheet. Herein, "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The absorbent core suitable for use in the present invention can be any liquid-absorbent material known in the art for use in absorbent articles, provided that the liquid-absorbent material can be configured or constructed to meet absorbent capacity requirements.

Non-limiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or crosslinked cellulose fibers; meltblown fibers; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof.

One suitable absorbent core material is an air-laid tissue material having a basis weight of 90 $g/m^2$ which is available from KNH, under Code No. A902.

D. Assembly

The topsheet, the backsheet, and the absorbent core can be assembled in a variety of configurations, sizes and shapes known in the art. Preferred configurations are described in U.S. Pat. Nos. 4,950,264 and 5,009,653 issued to Osborn; U.S. Pat. No. 4,425,130 issued to DesMarais; U.S. Pat. Nos. 4,589,876 and 4,687,478 issued to Van Tilburg; and U.S. Pat. 5,234,422 issued to Sneller, et al.

Methods of Treating the Body

The body of the wearer (e.g., the vulvar skin or other skin) is treated with the body treatment compositions which incorporates the condensed tannin. Generally, a safe and effective amount of the body treatment composition is applied to an absorbent article described herein wherein such safe and effective amounts include applying from about 0.0155 $g/m^2$ (about 0.01 $mg/in^2$) to about 310 $g/m^2$ (about 200 $mg/in^2$), from about 0.155 $g/m^2$ (about 0.1 $mg/in^2$) to about 155 $g/m^2$ (about 100 $mg/in^2$), from about 0.5 $g/m^2$ (about 0.003 $mg/in^2$) to about 93 $g/m^2$ (about 60 $mg/in^2$), of the body treatment composition to the absorbent article.

Typically, a safe and effective amount of the body treatment compositions is applied to an absorbent article (e.g., a sanitary napkin) such that at least about 0.0015 $g/cm^2$(about 0.001 $mg/in^2$) to about 310 $g/CM^2$ (about 200 $mg/in^2$), from about 0.006 $g/cm^2$ (about 0.004 mg/in2) to about 155 $g/cm^2$ (about 100 mg/in$^2$), from about 0.05 g/cm$^2$ (about 0.03 mg/in$^2$) to about 62 g/cm$^2$ (about 40 mg/in$^2$), of the composition is transferred to the body during a single use of an absorbent article which is typically about a two hour period.

Sanitary napkins are generally changed every two to five hours during the day and once for overnight use, resulting in at least a safe and effective amount of from about 0.0045 g/cm$^2$ (about 0.003 mg/in$^2$) to about 1860 g/cm$^2$ (about 1200 mg/in$^2$), from about 0.018 g/cm$^2$ (about 0.012 mg/in$^2$) to about 930 g/cm$^2$ (about 600 mg/in$^2$), from about 0.15 g/cm (about 0.09 mg/in$^2$) to about 372 g/cm$^2$ (about 240 mg/in$^2$), of the body treatment composition being administered within a one day interval (24 hour period). However, the transfer of the body treatment compositions onto a wearer's body via a sanitary napkin described herein can occur for one day, several days, weeks, months, or years at appropriate intervals provided that safe and effective amounts of the body treatment compositions are administered to deliver the body treatment benefits described herein.

The body treatment compositions may be applied to the absorbent articles by any known or otherwise effective technique for distributing a body treatment composition onto an absorbent article such as a sanitary napkin. Nonlimiting examples of methods of applying the body treatment compositions onto an absorbent article include spraying, printing (e.g., flexographic printing), coating (e.g., contact slot coating and gravure coating), extrusion, or combinations of these application techniques. The application of the skin care compositions onto an absorbent article facilitates the transfer or migration of the body treatment compositions onto the skin for administration and/or deposition of the body treatment compositions, resulting in a safe and effective amount of the compositions being applied for improved prevention and reduction of skin disorders. Therefore, the safe and effective amount of the body treatment composition that will transfer or migrate to the body will depend on factors such as the type of body treatment composition that is applied, the portion of the body contacting surface where the body treatment composition is applied, and the type of absorbent article used to administer the body treatment composition.

Any suitable method can be used in determining the amount of a body treatment composition described herein that is transferred to the body of a wearer during use of an absorbent article containing the composition. An example of specific methods for the calculation of transfer amounts of skin care compositions include Gas Chromatographic and other quantitative analytical procedures that involve the analysis of in vivo skin analog materials. A suitable Gas Chromatographic procedure is more fully described in International Publication No. WO 99/45973, published on Sep. 16, 1999.

EXAMPLES

Examples below are prepared by modifying a pantiliner product which is commercially available as "Subesube Cotton Sheet" by Procter & Gamble Far East, Inc. in Japan. This pantiliner product comprises a nonwoven topsheet having a leaf embossing pattern, a breathable microporous film backsheet, and an absorbent core comprising one layer of an air-laid tissue material disposed between the topsheet and the backsheet. This pantiliner product has a contour shape with gradually concaving sides and two ends each having a curved end edge. The peripheral edge of the pantiliner product is formed by a heat/pressure seal. This pantiliner product is manufactured and packaged by Kang Na Hsiung Enterprise Co., Ltd. (KNH), a Taiwan company.

Example I

The component fibers for the topsheet are bi-component fibers which are available from Chisso Corporation, Tokyo, Japan, under Code No. ESC052. An original finishing oil which is available from Sanyo Chemical Industries Ltd., Kyoto, Japan, under Code No. Sunoil F is prepared. A condensed tannin which is available from Rilis Scientific Industry Co., Ltd., Osaka, Japan, under Code No. Pancil COS-6A is dissolved in the finishing oil. The component fibers are treated with the resultant finishing oil by a touch roll process. After the resultant fibers are fried and cut into short fibers (i.e., the average length is about 51 mm), they are formed into a nonwoven web by a carded thermal bonding process (or an air-thru process). The resultant topsheet material has a basis weight of 18 g/m$^2$.

The absorbent core is formed by an air-laid tissue material which has a basis weight of 90 g/m$^2$ and is available from KNH, under Code No. A902.

The backsheet is formed by a microporous polyethylene film which has a basis weight of 37 g/m$^2$ and is available from Mitsubishi Plastics. Inc., Tokyo, Japan, under Code No. RN-13.

Example II

The compositions exemplified in Table 1 are representative of carrier systems (or materials) of the body treatment compositions. The carrier systems are generally prepared by combining, by weight, petrolatum and a fatty alcohol such as behenyl alcohol, and then heating the mixture while stirring to a temperature of about 80° C. using a low speed propeller mixer. Next, viscosity or thickening agents are added to the mixture to shear mix the ingredients into a final carrier system. Suitable viscosity or thickening agents include beheneth-10, fumed silica, bentonite, and steareth-2, wherein the viscosity or thickening agents are used alone or in combination. The ingredients can be shear mixed at 11,000 revolutions per minute (rpm) using an IKA Ultra Turrax Shear Mixer.

Alternatively, the petrolatum, fatty alcohol, and viscosity or thickening agent can be combined, heated with stirring at 80° C. to melt the ingredients, and then mixed into a final carrier system using a high speed blade mixer such as the Tokusyu Kika TK Robo Mics which operates at 5,000 rpm.

TABLE 1

| | Carrier Systems | | | | | | |
|---|---|---|---|---|---|---|---|
| Component | Sample 1 (Wt. %) | Sample 2 (Wt. %) | Sample 3 (Wt. %) | Sample 4 (Wt. %) | Sample 5 (Wt. %) | Sample 6 (Wt. %) | Sample 7 (Wt. %) |
| Petrolatum[1] | 78.1 | 67.8 | 70.0 | 70.0 | 70.0 | 73.5 | 85.0 |
| Behenyl Alcohol[2] | 8.7 | 29.0 | — | 20.0 | 15.0 | 20.0 | 15.0 |
| Cetearyl Alcohol[3] | — | — | 30.0 | — | — | — | — |
| Beheneth-10[4] | 10.0 | — | — | — | — | — | — |

TABLE 1-continued

Carrier Systems

| Component | Sample 1 (Wt. %) | Sample 2 (Wt. %) | Sample 3 (Wt. %) | Sample 4 (Wt. %) | Sample 5 (Wt. %) | Sample 6 (Wt. %) | Sample 7 (Wt. %) |
|---|---|---|---|---|---|---|---|
| Fumed Silica[5] | 3.2 | 3.2 | — | — | — | — | — |
| Bentonite[6] | — | — | — | 10.0 | — | — | — |
| Steareth-2[7] | — | — | — | — | 15.0 | — | — |
| Span 60[8] | — | — | — | — | — | 6.5 | — |

Wt. %—weight percent
[1] petrolatum available as Protopet ® 1S from the Witco Corporation
[2] behenyl alcohol available as Lanette 22 from the Cognis Corporation
[3] cetearyl alcohol available as Stenol 1822 from the Cognis Corporation
[4] beheneth-10 available as Mergital ® B10 from the Cognis Corporation
[5] fumed silica available as Cabosil ® TS-720 from the Cabot Corporation
[6] bentonite available as Bentone ® 38 from the Rheox Incorporation
[7] steareth-2 available as Brij ® 762 from the Uniqema Corporation
[8] sorbitan monostearate available as Span 60 from the Uniqema Corporation Examples II-IX The following Examples II-IX illustrated hereinbelow in Table 2 are representative of body treatment compositions that include the carrier systems identified in Table 1. The body treatment compositions are prepared by formulating a premix solution of the zinc oxide body treatment agent and adding the zinc oxide premix to the other body treatment agents and any optional ingredients such as panthenol and glycerin, or by formulating a body treatment solution of hexamidine and niacinamide skin treatment agents and any optional ingredients. The body treatment solution is then added to a carrier system such as those described in Table 1, wherein the body treatment solution and carrier system is heated while stirring to a temperature of about 80° C. All ingredients are included by weight of the body treatment compositions. These body treatment compositions are especially effective in the control of skin disorders such as skin erythema, malodor, and skin bacterial infections.

The body treatment composition of Example II is subsequently applied by spraying the composition onto the entire body surface wearer-contacting surface of the pantiliner. To deliver a safe and effective amount of the body treatment composition onto the skin, about 30 g/m$^2$ (19.5 mg/in$^2$) of the body treatment composition is applied to the topsheet using a hot melt pneumatic Dynatec E84B1758 spray head having a head operating temperature of about 90° C. and an atomization pressure of about 16 kiloPascals (kPa).

The body treatment composition of Example III is subsequently applied to a topsheet component of the pantiliner using a contact applicator such as a Nordson EP 11-12-02. The skin care composition is applied as alternating stripes having 4mm width. The topsheet is then assembled, with the composition on the body side surface, to form a pantiliner. To deliver a safe and effective amount of the body treatment composition onto the body, about 155 g/m$^2$ (100 mg/in$^2$) of the body treatment composition is applied to the topsheet.

TABLE 2

Body Treatment Compositions

| Component | Ex. II (Wt. %) | Ex. III (Wt. %) | Ex. IV (Wt. %) | Ex. V (Wt. %) | Ex. VI (Wt. %) | Ex. VII (Wt. %) | Ex VIII (Wt. %) | Ex IX (Wt. %) | Ex X (Wt. %) |
|---|---|---|---|---|---|---|---|---|---|
| Sample 1 | 97.0 | 89.3 | — | — | — | — | — | — | — |
| Sample 2 | — | — | 94.2 | 94.7 | — | — | — | — | — |
| Sample 3 | — | — | — | — | 95.6 | — | — | — | — |
| Sample 4 | — | — | — | — | — | 96.8 | — | — | — |
| Sample 5 | — | — | — | — | — | — | 95.8 | — | — |
| Sample 6 | — | — | — | — | — | — | — | 94.5 | — |
| Sample 7 | — | — | — | — | — | — | — | — | 99.95 |
| Apple tannin[9] | 0.1 | 0.5 | 2.0 | 5.0 | — | — | — | — | — |
| Persimmon tannin[10] | — | — | — | — | 0.1 | 0.5 | 2.0 | 5.0 | 0.05 |
| ZnO Premix[11] | 0.7 | 7.1 | 0.75 | 0.2 | — | — | — | — | — |
| Hexamidine[12] | 0.1 | 0.03 | 0.05 | 0.1 | 0.05 | 0.02 | 0.1 | — | — |
| Panthenol[13] | 0.5 | 0.5 | 0.5 | — | 0.5 | 0.25 | — | — | — |
| Glycerine[14] | 0.1 | — | — | — | — | — | 0.1 | — | — |
| Niacinamide[15] | 1.0 | 2.0 | 2.0 | — | — | — | 2.0 | — | — |
| Acidified Niacinamide[16] | — | — | — | — | 3.7 | 1.9 | — | — | — |
| Chamomile[17] | 0.5 | — | 0.5 | — | — | 0.5 | — | 0.5 | — |

[9] Apple tannin available as ApplePhenon from Asahi Food & Health Care Ltd.
[10] Persimmon tannin available as Pancil COS-6A from Rilis Scientific Industry Co., Ltd.,
[11] Zinc oxide premix comprising 70% zinc oxide mixture of ULTRAFINE 350 zinc oxide available from the Kobo Incorporation, Arlecel ® P100 available from the Uniqema Incorporation, and Salacos ® 99 available from the Ikeda Incorporation
[12] hexamidine available as hexamidine diisethionate from Laboratories Serolobilogiques under the tradename ELASTAB HP100
[13] panthenol available as D-panthenol from Roche Vitamins Incorporation
[14] glycerine available as Glycerine, USP Kosher ® from the Procter & Gamble Company
[15] niacinamide available from Em Industries HHN
[16] acidified niacinamide made by reacting niacinamide with stearic acid
[17] chamomile available as Phytoconcentrol Chamomile from Dragoco The body treatment composition of Example IV is subsequently applied to a topsheet component of the pantiliner using a contact applicator such as a Nordson EP 11-12-02. The topsheet is then assembled, with the composition on the body side surface, to form a pantiliner. To deliver a safe and effective amount of the body treatment composition onto the skin, about 0.5 g/m$^2$ (0.003 mg/in$^2$) of the body treatment composition is applied to the topsheet.

The body treatment composition of Example V is subsequently applied by spraying the composition onto the entire body surface wearer-contacting surface of the pantiliner. To deliver a safe and effective amount of the body treatment composition onto the body, about 60 g/m$^2$ (39 mg/in$^2$) of the body treatment composition is applied to the topsheet using a hot melt pneumatic Dynatec E84B1758 spray head having a head operating temperature of about 90° C. and an atomization pressure of about 16 kiloPascals (kPa).

The body treatment composition of Example VI is subsequently applied to a topsheet component of the pantiliner using a contact applicator such as a Nordson EP 11-12-02. The body treatment composition is applied as alternating stripes having 5mm width. The topsheet is then assembled, with the composition on the body side surface, to form a pantiliner. To deliver a safe and effective amount of the body treatment composition onto the body, about 310 g/m$^2$ (200 mg/in$^2$) of the body treatment composition is applied to the topsheet.

The body treatment composition of Example VII is subsequently applied to a topsheet component of the pantiliner using a contact applicator such as a Nordson EP 11-12-02. The body treatment composition is applied as alternating stripes having 3mm width. The topsheet is then assembled, with the composition on the body side surface, to form a pantiliner. To deliver a safe and effective amount of the body treatment composition onto the body, about 5 g/m$^2$ (0.03 mg/in$^2$) of the body treatment composition is applied to the topsheet.

The body treatment composition of Example VIII is subsequently applied by spraying the composition onto the entire body surface wearer-contacting surface of the pantiliner. To deliver a safe and effective amount of the body treatment composition onto the body, about 10 g/m$^2$ (0.06 mg/in$^2$) of the body treatment composition is applied to the topsheet using a hot melt pneumatic Dynatec E84B1758 spray head having a head operating temperature of about 90° C. and an atomization pressure of about 16 kiloPascals (kPa).

The body treatment composition of Example IX is subsequently applied by slot coating (Nordson EP 11-12-02) striped configurations of the composition onto the wearer-contacting surface of a hydrophobic spunbond bicomponent polyethylene/polypropylene topsheet (BBA, Washougal, WA) of the pantiliner. To deliver a safe and effective amount of the body treatment composition onto the body, the body treatment composition is applied to the topsheet in a striped configuration wherein the striped configuration comprises at least two stripes each being 5 millimeters (mm) wide ×60 mm long and having about 20 g/cm$^2$ (0.12 mg/in$^2$) of the composition applied thereon. The topsheet is then assembled, with the composition on the body side surface, to form a pantiliner.

The body treatment composition of Example X is subsequently applied by spraying the composition onto the entire body surface wearer-contacting surface of the pantiliner. To deliver a safe and effective amount of the body treatment composition onto the body, about 3.3 g/m$^2$ (0.02 mg/in$^2$) of the body treatment composition is applied to the topsheet using a hot melt pneumatic Dynatec E84B1758 spray head having a head operating temperature of about 90 ° C. and an atomization pressure of about 16 kiloPascals (kPa).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a condensed tannin, wherein the condensed tannin is extracted from a plant family which is selected from the group consisting of Ebenacea, Mimosoideae, Apiaceae, Pinaceae, Rosaceae, Fagaceae, and mixtures thereof;

wherein the absorbent article further comprises a carrier material for the condensed tannin; and wherein the carrier material is a component treatment material for controlling the physical property of a component material of the absorbent article.

2. The absorbent article of the claim 1, wherein the absorbent article includes a topsheet; a backsheet; and an absorbent core disposed between the topsheet and the backsheet; and wherein at least one of the topsheet, the backsheet and the absorbent core includes the condensed tannin.

3. The absorbent article of the claim 2, wherein at least one of the topsheet, the backsheet and the absorbent core includes component fibers.

4. The absorbent article of the claim 3, wherein the component fibers have a surface treated with the condensed tannin.

5. The absorbent article of the claim 3, wherein the component fibers include a thermoplastic material which contains the condensed tannin.

6. The absorbent article of the claim 2, wherein at least one of the topsheet, the backsheet and the absorbent core includes a sheet material having a surface treated with the condensed tannin.

7. The absorbent article of the claim 6, wherein the topsheet includes the sheet material which is an apertured formed film having a surface treated with the condensed tannin.

8. The absorbent article of the claim 1, wherein the carrier material is a body treatment material for the wearer's body which delivers the condensed tannin to at least a portion of the body of the wearer of the article.

9. The absorbent article of the claim 1, wherein the condensed tannin is a persimmon tannin that has the following structure:

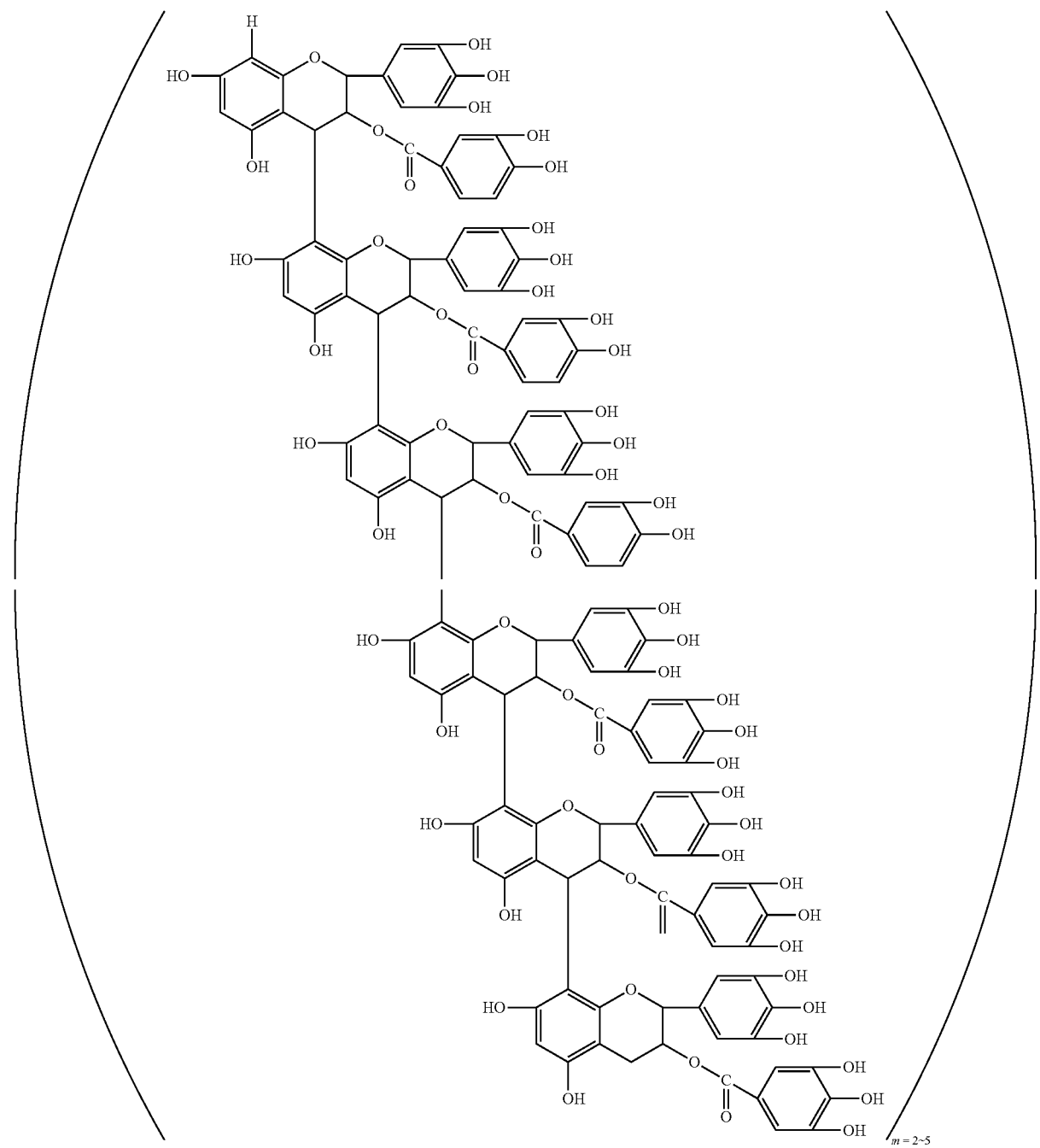

10. The absorbent article of the claim 1, wherein the condensed tannin is an apple tannin that has the following structure:

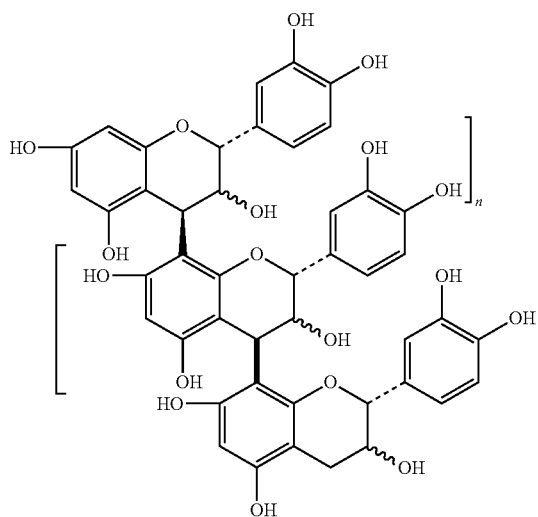

11. The absorbent article of the claim 1, wherein the absorbent article is a sanitary napkin or a pantiliner.

12. An absorbent article comprising a condensed tannin, wherein the condensed tannin is extracted from a plant family which is selected from the group consisting of Ebenacea, Mimosoideae, Apiaceae, Pinaceae, Rosaceae, Fagaceae, and mixtures thereof;

wherein the absorbent article further comprises a carrier material for the condensed tannin; and wherein the carrier material is a body treatment material for the wearer's body which delivers the condensed tannin to at least a portion of the body of the wearer of the article.

13. The absorbent article of the claim 12, wherein the absorbent article includes a topsheet; a backsheet; and an absorbent core disposed between the topsheet and the backsheet; and wherein at least one of the topsheet, the backsheet and the absorbent core includes the condensed tannin.

14. The absorbent article of the claim 13, wherein at least one of the topsheet, the backsheet and the absorbent core includes component fibers.

15. The absorbent article of the claim 14, wherein the component fibers have a surface treated with the condensed tannin.

16. The absorbent article of the claim 14, wherein the component fibers include a thermoplastic material which contains the condensed tannin.

17. The absorbent article of the claim 13, wherein at least one of the topsheet, the backsheet and the absorbent core includes a sheet material having a surface treated with the condensed tannin.

18. The absorbent article of the claim 17, wherein the topsheet includes the sheet material which is an apertured formed film having a surface treated with the condensed tannin.

19. The absorbent article of the claim 12, wherein the condensed tannin is a persimmon tannin that has the following structure:

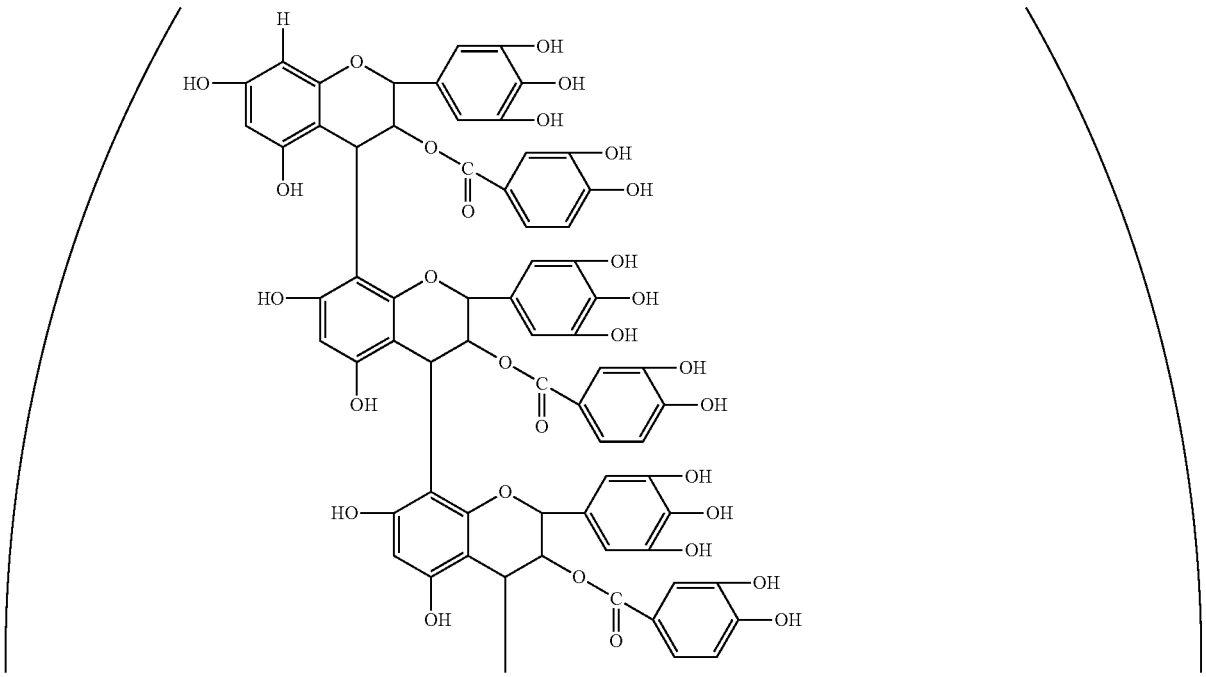

-continued
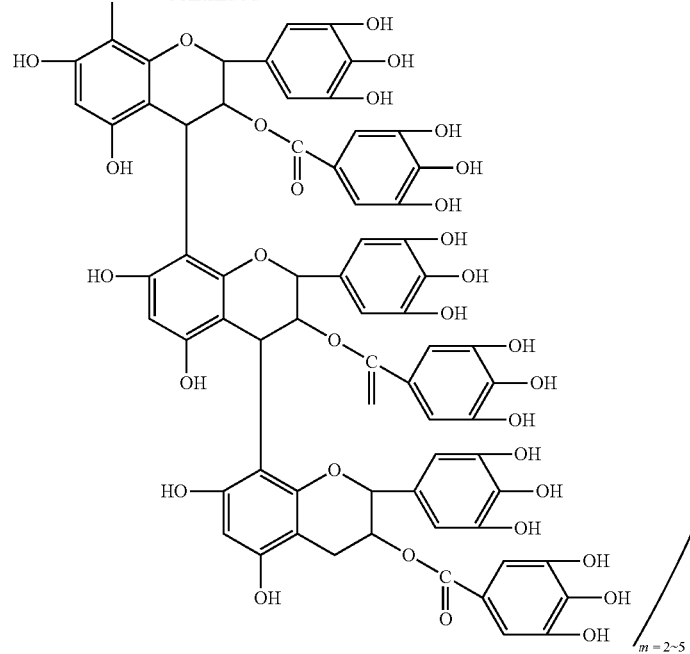
20. The absorbent article of the claim 12, wherein the condensed tannin is an apple tannin that has the following structure:
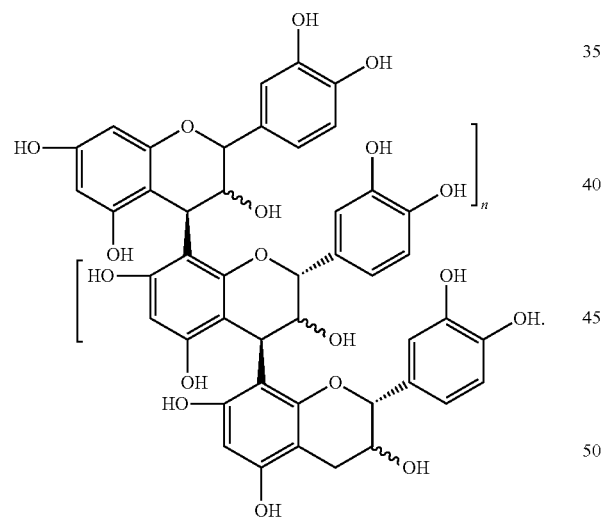
* * * * *